(12) United States Patent
Ramirez

(10) Patent No.: US 9,884,008 B2
(45) Date of Patent: *Feb. 6, 2018

(54) DENTAL CLEANING COMPOSITION

(71) Applicant: JR CHEM, LLC, Miami, FL (US)

(72) Inventor: Jose E Ramirez, Milford, CT (US)

(73) Assignee: JR CHEM, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,542

(22) Filed: Nov. 25, 2014

(65) Prior Publication Data

US 2015/0182445 A1  Jul. 2, 2015

Related U.S. Application Data

(62) Division of application No. 13/338,417, filed on Dec. 28, 2011, now Pat. No. 8,900,557.

(60) Provisional application No. 61/428,562, filed on Dec. 30, 2010.

(51) Int. Cl.
| A61K 8/97 | (2017.01) |
| A61K 8/49 | (2006.01) |
| A61Q 11/00 | (2006.01) |
| A61K 8/30 | (2006.01) |
| A61K 8/19 | (2006.01) |
| A61K 8/22 | (2006.01) |

(52) U.S. Cl.
CPC .............. *A61K 8/97* (2013.01); *A61K 8/19* (2013.01); *A61K 8/22* (2013.01); *A61K 8/30* (2013.01); *A61K 8/4973* (2013.01); *A61Q 11/00* (2013.01); *A61K 2800/522* (2013.01)

(58) Field of Classification Search
USPC .............................................. 424/48, 49, 54
See application file for complete search history.

(56) References Cited

U.S. PATENT DOCUMENTS

| 2,946,725 A | 7/1960 | Norris et al. |
| 3,070,510 A | 12/1962 | Cooley et al. |
| 3,535,421 A | 10/1970 | Briner et al. |
| 3,538,230 A | 11/1970 | Pader et al. |
| 3,678,154 A | 7/1972 | Widder et al. |
| 3,882,228 A | 5/1975 | Boncey et al. |
| 3,885,029 A * | 5/1975 | Norfleet ................. A61K 8/24 424/52 |
| 3,959,458 A | 5/1976 | Agricola et al. |
| 3,988,433 A | 10/1976 | Benedict |
| 4,051,234 A | 9/1977 | Gieske et al. |
| 4,083,955 A | 4/1978 | Grabenstetter |
| 4,115,293 A | 9/1978 | Schoenholz et al. |
| 4,136,163 A | 1/1979 | Watson et al. |
| 4,138,477 A | 2/1979 | Gaffar |
| 4,183,914 A | 1/1980 | Gaffar et al. |
| 4,206,215 A | 6/1980 | Bailey |
| 4,264,592 A * | 4/1981 | Xhajanka ................. A61K 8/97 424/401 |
| 4,305,502 A | 12/1981 | Gregory et al. |
| 4,340,583 A | 7/1982 | Wason |
| 4,371,516 A | 2/1983 | Gregory et al. |
| 4,443,430 A | 4/1984 | Mattei |
| 4,459,425 A | 7/1984 | Amano et al. |
| 4,525,343 A * | 6/1985 | Raaf .............................. 424/54 |
| 4,528,180 A | 7/1985 | Schaffer |
| 4,642,903 A | 2/1987 | Davies |
| 4,687,662 A | 8/1987 | Schobel |
| 4,849,213 A | 7/1989 | Schaeffer |
| 4,894,220 A | 1/1990 | Nabi et al. |
| 4,946,684 A | 8/1990 | Blank et al. |
| 5,015,466 A | 5/1991 | Parran et al. |
| 5,180,577 A | 1/1993 | Polefka et al. |
| 5,188,825 A | 2/1993 | Iles et al. |
| 5,198,220 A | 3/1993 | Damani |
| 5,213,790 A | 5/1993 | Lukacovic et al. |
| 5,215,756 A | 6/1993 | Gole et al. |
| 5,242,910 A | 9/1993 | Damani |
| 5,281,410 A | 1/1994 | Lukacovic et al. |
| 5,298,261 A | 3/1994 | Pebley et al. |
| 5,370,864 A | 12/1994 | Peterson et al. |
| 5,575,654 A | 11/1996 | Fontenot |
| 5,589,160 A | 12/1996 | Rice |
| 5,603,920 A | 2/1997 | Rice |
| 5,651,958 A | 7/1997 | Rice |
| 5,658,553 A | 8/1997 | Rice |
| 5,766,574 A | 6/1998 | Beck et al. |
| 5,814,304 A | 9/1998 | Wong et al. |
| 5,851,514 A | 12/1998 | Hassan et al. |
| 5,952,384 A | 9/1999 | Katz |
| 6,682,722 B2 | 1/2004 | Majeti et al. |
| 6,705,328 B1 | 3/2004 | Ramirez |
| 6,908,607 B2 | 6/2005 | Banerjee et al. |
| 7,172,632 B2 | 2/2007 | Smith et al. |
| 2009/0082316 A1 | 3/2009 | Cimiluca et al. |

FOREIGN PATENT DOCUMENTS

| FR | 2715842 | * | 8/1995 | ............... A61K 7/26 |
| RU | 1796180 | * | 2/1993 | |
| WO | WO1999021570 | * | 5/1999 | ............... A23L 1/30 |

OTHER PUBLICATIONS

Sano, et al. "Determining Peroxyl Radical Scavenging Activity", J. Agric Food Chem. vol. 51, No. 10, pp. 2913-2915 (2003).
"Antioxidant Capacity of Tea and Vegetables", J. Agric Food Chem. vol. 44, No. 11, pp. 3427 and 3429, (1996).

(Continued)

*Primary Examiner* — Walter Webb
(74) *Attorney, Agent, or Firm* — Perman & Green, LLP

(57) ABSTRACT

Provided are dental cleaning compositions, methods of using and methods of using such compositions which minimize gum damage in the oral cavity. In one form, the dental cleaning composition includes a substantially stoichiometric ratio of one or more oxidizing agents to one or more reducing agents in one or more one or more orally acceptable carriers; where the substantially stoichiometric ratio of one or more oxidizing agents to one or more reducing agents is sufficient to neutralize the oxidizing agent in a subject oral cavity; and where the one or more oxidizing agents and one or more reducing agents are either co-dispensed or sequentially dispensed in the subject oral cavity.

17 Claims, No Drawings

(56) References Cited

OTHER PUBLICATIONS

Wang, et al. "Effect of Acetone Extraction Time (Table 1)" and "ORAC of Selected Fruits Using AAPH . . . (Table 2)" J. Agric. Food Chem. vol. 44, No. 3, p. 702, (1996).
"Antioxidant Capacity of Natural Polyphenols" J. Agric. Food Chem. vol. 50, No. 26, p. 7507 (2002).
Song, et al. "CAA Values of Selected Vegetables in the (A) . . . (Figure 3)" J. Argic. Food Chem., vol. 58, No. 11, p. 6624 (2010).

* cited by examiner

DENTAL CLEANING COMPOSITION

CROSS REFERENCE TO RELATED APPLICATIONS

This application is a divisional application filed under 37 C.F.R. 1.53(b) of parent application serial number U.S. Ser. No. 13/338,417, filed on Dec. 28, 2011, the entirety of which is hereby incorporated herein by reference, which claims the benefit of provisional patent application Ser. No. 61/428,562 filed on Dec. 30, 2010, the disclosure of which is also incorporated by reference herein in its entirety.

BACKGROUND

1. Field

The present disclosure relates to the field of dental cleaning. It more particularly relates to novel dental cleaning compositions, methods of making the compositions and methods of applying the compositions that do not damage the gums of the oral cavity. In particular, these benefits are achieved by applying compositions comprising a combination of an oxidizing agent and a reducing agent in one or more orally acceptable carriers which are either co-dispensed or sequentially dispensed.

2. Brief Description of Related Developments

The formation of dental plaque and calculus is the primary source of dental caries, gingivitis, periodontal disease, and tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many as 400 different varieties of microorganisms. This mix includes both aerobic and anaerobic bacteria, fungi, and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans, and microorganisms form an adhesive skeleton for the continued proliferation of plaque.

Dental calculus, or tartar, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars. Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of unless stained or discolored by some extraneous agent. In addition to being unsightly and undesirable from an aesthetic standpoint, the mature calculus deposits are constant sources of irritation of the gingiva.

The failure to retard or stop the proliferation of plaque and calculus is detrimental to oral health. Plaque and calculus formation may lead to dental caries, gingival inflammation, periodontal disease, and ultimately tooth loss. Acidified dental preparations (pH lower than 7) have been shown to be good plaque and calculus dissolving agents. However, the potential damage of using regular organic or strong organic acids has kept them from being used in commercial products. Additionally, calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of stain promoting oral products, such as chlorhexidine.

Conventional dental cleaning compositions typically contain a peroxide-bleaching agent in combination with a stabilizer and other additives. The stabilizer functions to inhibit the breakdown of the peroxide bleaching agent by slowing down the dissociation of the peroxide thereby prolonging its potency over a longer period of storage prior to use. The problem with conventional dental cleaning compositions is that they cause damage the cells of the gums of the oral cavity by reactive oxygen species. An important example of such damage is lipid peroxidation which involves the oxidative degradation of unsaturated lipids. Lipid peroxidation is highly detrimental to membrane structure and function and can cause numerous cytopathological effects. Cells defend against lipid peroxidation by producing radical scavengers such as superoxide dismutase, catalase, and peroxidase. Injured cells have a decreased ability to produce radical scavengers. Excess hydrogen peroxide can react with DNA to cause backbone breakage, produce mutations, and alter and liberate bases. Hydrogen peroxide can also react with pyrimidines to open the 5,6-double bond. This reaction inhibits the ability of pyrimidines to hydrogen bond to complementary bases, Hallaender et al. (1971). Such oxidative biochemical injury can result in the loss of cellular membrane integrity, reduced enzyme activity, changes in transport kinetics, changes in membrane lipid content, and leakage of potassium ions, amino acids, and other cellular material. In addition, the production of reactive oxygen intermediates has been suggested to cause many tissue disorders, such as cytotoxicity, skin inflammation, gum shrinkage, etc.

A need exists for improved dental cleaning compositions that are not only effective in whitening the teeth, but also do not cause damage to the gums, and help remove calculus and tartar without damaging the enamel.

DETAILED DESCRIPTION

Definitions:

All numerical values within the detailed description and the claims herein are modified by "about" or "approximately" the indicated value, and take into account experimental error and variations that would be expected by a person having ordinary skill in the art.

All documents cited are, in relevant part, incorporated herein by reference; the citation of any document is not to be construed as an admission that it is prior art with respect to the present disclosure. All percentages and ratios used herein are by weight of the specific dental cleaning composition and not of the overall dental whitening formulation that is delivered, unless otherwise specified. All measurements are made at 25° C., unless otherwise specified.

The term "comprising" means that other steps and other ingredients which do not affect the end result can be added.

By "dental cleaning composition" is meant a product which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity and the cleaning, stain removal and whitening of teeth within the oral cavity. The dental cleaning composition of the present disclosure may be in the form of a toothpaste, dentifrice, tooth powder, topical oral gel, mouth rinse, denture product, mouth spray, lozenge, oral tablet, chewing gum, dental floss, or combinations thereof.

The term "dentifrice", as used herein, means paste, gel, or liquid formulations unless otherwise specified. The dentifrice composition may be a single phase composition or may be a combination of two or more dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing toothpaste or dental floss.

The term "teeth", as used herein, refers to natural teeth as well as artificial teeth or dental prosthesis.

The term "orally acceptable carrier" as used herein means any safe and effective materials for use in the compositions of the present disclosure. Such materials include fluoride ion sources, additional anticalculus agents, buffers, abrasive polishing materials, peroxide sources, alkali metal bicarbonate salts, thickening materials, humectants, water, surfactants, titanium dioxide, flavor system, sweetening agents, xylitol, coloring agents, and mixtures thereof.

Pellicle is the protein film that forms on the surface of the enamel by selective binding of glycol proteins.

Herein, the terms "tartar" and "calculus" are used interchangeably and refer to mineralized dental plaque deposits.

The term "minimal gum damage" as used herein means that the gums of the oral cavity are not significantly irritated or otherwise significantly weakened by the application of the dental cleaning compositions of the present disclosure.

The term "minimal enamel damage" as used herein means that the enamel surface of the teeth in the oral cavity is not significantly damage or otherwise significantly weakened by the application of the dental cleaning compositions of the present disclosure.

The term "substantially stoichiometric" as used herein means that the ratio of the one or more oxidizing agents to the one or more reducing agents in the dental cleaning compositions is such that quantity of reducing agents is sufficient to react with and neutralize substantially all of the oxidizing agents present in the composition in a subject oral cavity. However, "substantially stoichiometric" also means there may be an excess of reducing agents relative to oxidizing agents in the compositions, that is 1 wt. % or more, or 2 wt. % or more, or 5 wt. % or more, or 7 wt. % or more, or 10 wt. % or more of excessive reducing agent to oxidizing agent that would also be sufficient to neutralize substantially all of the oxidizing agents present in the composition in a subject oral cavity.

Overall Description:

The present invention relates to dental cleaning compositions used to clean teeth in the oral cavity of a human or animal, methods of making such compositions and methods of using such compositions.

The dental cleaning compositions disclosed herein, which are used to clean, remove stains and whiten teeth via an oxidative type mechanism, may be in the form of a two component composition. One component carries one or more oxidizing agents (such as hydrogen peroxide), and the component carries one or more reducing agents (antioxidants).

Prior art compositions used to clean and whiten the teeth have various disadvantages, including, but not limited to gum damage and enamel damage due to the oxidative nature of the process. Therefore it is an object of the present invention to overcome some or all of the aforementioned disadvantages, and in particular to provide dental cleaning compositions which are gentler and milder to the teeth, gums and oral cavity.

According to the present disclosure, there is provided a dental cleaning composition containing at least one oxidative cleaning (also referred to as an oxidizing agent) and at least one reducing agent (also referred to as an antioxidant).

In the process of cleaning and whitening teeth, it is required to oxidize the surface of the teeth. Hydrogen peroxide is an example of such an oxidant, and is used to initiate the oxidation. Also susceptible to oxidation are the gums and teeth enamel of the oral cavity. Oxidation of the gums may lead to a reduction in gum strength, and hence damage. The oxidation of the teeth and gums can follow a chain reaction mechanism, by which hydrogen peroxide is the initiator. The hydrogen peroxide molecules degenerate into reactive oxygen species, which are free radicals, and rapidly start the chain reactions mentioned previously.

The applicant has discovered that one way of preventing the oxidative damage to the gums and enamel would be to use free radical scavenging agents, e.g. reducing agents or antioxidants, to mop up the reactive oxygen species, preventing the chain reactions. A disadvantage would be that the free radical scavengers may also mop up the reactive oxidative intermediate once they had been oxidized, and this would prevent further whitening and cleaning of the teeth.

To overcome this problem, the present disclosure is used. The present disclosure relates to the use of reducing agents and more particularly antioxidants that may be referred to as "chain-breaking", since they are believed to block the chain reactions mentioned above from developing far enough to damage the gums and the enamel of the teeth, but do not inhibit the cleaning, stain removal and whitening of the teeth by mopping up the reactive radical oxidizing agent molecules after oxidation. Incorporation into the dental cleaning formulation of the "chain-breaking" reducing agents/antioxidants has been shown to reduce considerably and significantly the level of gum and enamel damage.

The dental cleaning composition according to the present disclosure may contain a single one of the chain-breaking reducing agents/antioxidants. However, the reducing agents/antioxidants have shown significant synergistic action in combination with each other, enhancing the protection of the gums and enamel of the teeth against oxidative damage. This action is shown to be present with no adverse effect on the cleaning, stain removal and whitening of the teeth.

Various Aspects of the Disclosed Embodiment:

The present disclosure provides novel dental cleaning compositions, methods of making such compositions and methods of applying such compositions to the teeth. The compositions are distinguishable over the prior art in providing a combination of an oxidizing agent(s) and a reducing agent(s) in one or more orally acceptable carriers, which are either co-dispensed or sequentially dispensed and minimize gum damage associated with conventional dental cleaning compositions.

In one exemplary aspect of the present disclosure, the dental cleaning composition includes a substantially stoichiometric ratio of one or more oxidizing agents to one or more reducing agents in one or more orally acceptable carriers, wherein the oxidizing agent and reducing agent of the dental composition are either co-dispensed or sequentially dispensed.

In another exemplary aspect of the present disclosure, the dental cleaning composition includes 0.5 to 90 wt. % of one or more reducing agents in one or more orally acceptable carriers, wherein the one or more reducing agents are chosen from good grade antioxidants.

In an alternative aspect of the present disclosure, the method for whitening teeth includes: providing a dental cleaning composition including a substantially stoichiometric ratio of one or more oxidizing agents to one or more reducing agents in one or more orally acceptable carriers, and applying the dental cleaning composition to the oral cavity in a form chosen from a toothpaste, dentifrice, tooth powder, topical oral gel, mouth rinse, denture product, mouth spray, lozenge, oral tablet, or chewing gum, impregnated dental implement, and combinations thereof, wherein the oxidizing agent and reducing agent of the dental composition are either co-dispensed or sequentially dispensed.

In another exemplary aspect of the present disclosure, a method of making the dental cleaning composition includes providing a substantially stoichiometric ratio of one or more oxidizing agents, one or more reducing agents, and one or more orally acceptable carriers, mixing the one or more oxidizing agents into one or more orally acceptable carriers, mixing the one or more reducing agents into one or more orally acceptable carriers, and combining the mixture of the one or more oxidizing agents in one or more orally acceptable carriers and the mixture of the one or more reducing agents in one or more orally acceptable carriers in a form for either co-dispensing or sequentially dispensing, and wherein the form for either co-dispensing or sequentially dispensing the dental cleaning composition to an oral cavity is chosen from a toothpaste, dentifrice, tooth powder, topical oral gel, mouth rinse, denture product, mouth spray, lozenge, oral tablet, chewing gum, impregnated dental implement, and combinations thereof.

Oxidizing Agents:

The oxidizing agent functions primarily to whiten the teeth and is also commonly referred to as a teeth whitening actives. The oxidizing agents suitable for the dental cleaning compositions of the present disclosure include peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite. The preferred chlorite is sodium chlorite. Additional oxidizing agents may be hypochlorite and chlorine dioxide. A preferred percarbonate is sodium percarbonate. Other suitable oxidizing agents include potassium, ammonium, sodium and lithium persulfates and perborate mono- and tetrahydrates, and sodium pyrophosphate peroxyhydrate. In addition, a combination of the one or more oxidizing agents as described above may be used in the dental cleaning composition disclosed herein.

Dental bleaching compositions including peroxide bleaching (oxidizing) agents are further described in U.S. Pat. No. 6,908,607, herein incorporated by reference in its entirety.

Reducing Agents:

The reducing agent of the present disclosure is an element or compound in a reduction-oxidation reaction that donates an electron to the one or more oxidizing agents. The one or more reducing agents function primarily to neutralize and/or terminate the oxidizing agent(s) and therefore to help minimize gum damage. The reducing agent may be water soluble or non-water (oil) soluble. Non-limiting exemplary reducing agents suitable for neutralizing the one or more oxidizing agents of the present disclosure include lithium aluminium hydride ($LiAlH_4$), nascent hydrogen, sodium amalgam, sodium borohydride ($NaBH_4$), compounds containing the $Sn^{2+}$ ion, such as tin(II) chloride, compounds containing bismuth ions (bismuth compounds), sulfite compounds, hydrazine (Wolff-Kishner reduction), diisobutylaluminum hydride (DIBAH), Lindlar catalyst, ascorbic acid and ascorbyl glycoside (Vitamin C), phosphites, hypophosphites and phosphorous acid, dithiothreitol (DTT), and compounds containing the $Fe^{2+}$ ion, such as iron(II) sulfate, and combinations thereof.

Other suitable reducing agents include antioxidants. Antioxidants are molecules capable of inhibiting the oxidation of other molecules. Oxidation is a chemical reaction that transfers electrons from a substance to an oxidizing agent. Oxidation reactions can produce free radicals. In turn, these radicals can start chain reactions that damage cells and in particular the gums of the oral cavity when used as whitening agents. Antioxidants terminate these chain reactions by removing free radical intermediates, and inhibit other oxidation reactions, which may damage the gums of the oral cavity. Antioxidants function by being oxidized themselves, so antioxidants are often reducing agents. Antioxidants are classified into two broad divisions, depending on whether they are soluble in water (hydrophilic) or in lipids (hydrophobic). For food grade antioxidants, the oxygen radical absorbance capacity (ORAC) in vitro provides an artificial index of antioxidant strength. Vitamins A, C and E have antioxidant efficacy in vivo. A food "rich in antioxidants" typically means at least a ORAC rating of 1000 per 100 g.

Non-limiting exemplary antioxidants suitable for the one or more reducing agents of the present disclosure are as follows: selenium, zinc, ascorbic acid (Vitamin C), polyphenols (gallic acid, pyrogallol, quercetin, ethyl gallate, naringenin, luteolin, hesperidin, catechins), uric acid, lipoic acid, melatonin, glutathione, polyphenols, α-tocopherols and tocotrienols (Vitamin E), thiols, Vitamin A, carotenes, Vitamin D, ubiquinol (coenzyme Q), propyl gallate (PG, E310), tertiary butylhydroquinone (TBHQ), butylated hydroxyanisole (BHA, E320), butylated hydroxytoluene (BHT, E321), and combinations thereof.

Non-limiting exemplary catechins include epigallocatechin-3-O-gallate (EGCG), epicatechin-3-O-gallate (ECG), epigallocatechin (EGC), epicatechin (EC), epigallocatechin-3-O-(3-O-methyl)gallate (EGC3"Me), epigallocatechin-3-O-(4-O-methyl)gallate (EGC4"Me), 4'-O-Methyl epigallocatechin-3-O-gallate (EGCG4'Me), 4'-O-Methyl epigallocatechin-3-O-(4-O-methyl)gallate (EGCG4', 4"diMe), epigallocatechin-3-O-(3,4-O-dimethyl)gallate (EGCG3",4"diMe), epicatechin-3-O-(3-O-methyl)gallate (ECG3"Me), epicatechin-3-O-(4-O-methyl)gallate (ECG4"Me), 4'-O-Methyl epicatechin-3-O-gallate (ECG4'Me), 3'-O-Methyl epicatechin-3-O-(4-O-methyl)gallate(ECG3'4"diMe), 4'-O-Methyl epicatechin-3-O-(4-O-methyl)gallate (ECG4'4"diMe), epicatechin-3-O-(3,4-O-dimethyl)gallate (ECG3",4"diMe), gallocatechin (GC), catechin (C), gallocatechin-3-O-(3-O-methyl)gallate (GCG3"Me), and gallocatechin-3-O-(4-O-methyl)gallate (GCG4"Me).

Other exemplary antioxidants suitable with the dental cleansing composition disclosed herein include rosmarinic acid, cynarin, cyanidin 3-O-β-glucopyranoside, echinacoside, puerarin, and oleuropein.

One preferred form of Vitamin C for use in the composition is as ascorbic acid or the equivalent of a salt of ascorbic acid or the equivalent of a derivative of ascorbic acid. The vitamin C may either be in an immediate release form or a sustained release form.

Vitamin A (retinol) and carotene can be obtained from either animal or vegetable sources. The vitamin A can be in the form of vitamin A, retinol, retinyl palmitate, retinyl acetate, retinyl propriante, beta-carotene, alpha carotene, beta-cryptoxanthin, and mixtures thereof.

Nonlimiting examples of Vitamin D suitable for the present disclosure include Vitamin D3 (cholecalciferol), Vitamin D2 (ergocalciferol) and combinations thereof. Additional, nonlimiting examples also include metabolites of Vitamin D, including calcidiol, calcitriol, and combinations thereof. The Vitamin D, including cholecalciferol, ergocalciferol, calcidiol and calcitriol, may be derived from synthetic or natural sources. Vitamin D, including cholecalciferol and calcitriol, may be sourced from an extract of *solanum glaucophyllum* (malacoxylon), *trisetum flavescens* (goldhafer) or *cestrum diurnum*. Both the pure, Vitamin D and/or glycosides of the Vitamin D may be used.

In another form of the present disclosure, natural antioxidants may be used, including, but not limited to the following: lemon peel powder, grapefruit peel powder, melon peel powder, honeydew peel powder, pomegranate peel powder, *papaya* peel powder, or any other fruit with a sufficiently hard peel such that it can be processed into an abrasive powder. The abrasive powder preferably has a Mohs scale hardness rating of 1.5 to 5.0, or 2.0 to 4.5, or more advantageously less than 2.5 in order to avoid gum damage. Dried fruits are also a goods source of antioxidants and include, but are not limited to, raisins, figs, dates, blueberry, cranberry, blackberry, prune, raspberry, strawberry, apple, pecan, cherry, plum, pear, guava, mango, grapes, blackcurrant, orange, peach, cantaloupe, apricots, and kiwi. Good grade (Generally recognized as safe (GRAS) grades) antioxidants are preferable. These natural antioxidants derived from fruits may be produced by a freeze drying process to form concentrated extracts. These natural antioxidants may also function as abrasive and/or cleaning agents, and in particular, when formed from a fruit with a sufficiently hard peel. These antioxidants have the functional capacity to remove calculas and plaque according to the American Dental Association (ADA) accepted test methods.

The natural antioxidants suitable for use with the dental cleaning composition disclosed herein may be vegetable based, and include, but not limited to the following: beet, red pepper, eggplant, brussels sprout, broccoli, cabbage, mushroom, asparagus, green pepper, cauliflower, spinach, carrot, chili pepper, sweet potato, radish, yellow onion, lettuce, potato, sweet corn, white onion, squash, celery, zucchini, romaine lettuce, green pea, beetroot, avocado, green, bean, cucumber, broccoli rape, corn, garlic, kale, iceberg lettuce, leaf lettuce, broccoli flowers, artichoke, alfalfa sprouts, cherry-tomato, chive, red bean, kidney bean, black bean, pinto bean, russet potato, and asparagus. These vegetables may be produced by a freeze drying process to form concentrated extracts for use in the dental cleaning composition disclosed herein.

Other natural antioxidants suitable for use with the dental cleaning composition disclosed herein may also include herbal botanical extracts, such as green tea and black tea extracts.

Other vitamin cofactors and minerals suitable for antioxidants include coenzyme manganese, selenium, tin, bismuth, and manganese. Hormones suitable for antioxidants includes melatonin, Carotenoid terpenoids suitable for antioxidants include alpha-carotene, astaxanthin, beta-carotene, canthaxanthin, lutein, lycopene, and zeaxanthin. Flavonoid polyphenolics suitable for antioxidants include flavones (apigenin, luteolin, tangeritin), flavonols (isorhamnetin, kaempferol, myricetin, proanthocyanidins, condensed tannins, quercetin, rutin), flavanones (eriodictyol, hesperetin, naringenin), flavanols and their polymers (catechin, gallocatechin and corresponding gallate esters, epicatechin, epigallochtechin and corresponding gallate esters, theaflavin and its gallate esters, thearubigins), isoflavone phytoestrogens (daidzein, genistein, glycitein), stilbenoids (reservatrol, pterostilibene) and anthocyanins (cyanidin, delphinidin, malvidin, pelargonidin, peonidin, petunidin). Phenolic acids and their esters suitable for antioxidants include chicoric acid, chlorogenic acid, cinnamic acid and its derivatives, such as ferulic acid, ellagic acid, ellagitannins, gallic acid, gallotannins, rosmarinic acid, and salicyclic acid. Other nonflavonoid phenolics suitable as antioxidants include curcumin, flavonolignans, xanthones and eugenol. Other potential organic antioxidants include bilirubin, citric acid, oxalic acid, phytic acid, n-acetylcysteine (water soluble), R-α-lipoic acid (fat and water soluble) and uric acid.

A good source of polyphenol antioxidants are nuts, including, but not limited to, pecans, walnuts, hazelnuts, pistachio, almond, cashew nut, macadamia nut and peanuts.

Spices may also be used as antioxidants including, but not limited to, clove, cinnamon, oregano, turmeric, cumin, parsley, basil, curry powder, mustard seed, ginger, pepper, chili powder, paprika, garlic, coriander, onion and cardamom.

Herbs may also be used as antioxidants including, but not limited to, sage, thyme, marjoram, tarragon, peppermint, oregano, savory, basil and dill weed.

Co-dispensing and Sequential Dispensing of Dental Cleaning Composition:

The dental cleaning composition of the present disclosure may be in the form of a dentifrice, toothpaste, tooth powder, topical oral gel, mouth rinse, denture product, mouth spray, lozenge, oral tablet, chewing gum, dental floss, or combinations thereof.

The dental cleaning compositions of the present disclosure may have a pH ranging from 4 to 10, or 4 to 9, or 6 to 9, or 4 to 8, or 6 to 8, or 7 to 8.

The one or more oxidizing agents and one or more reducing agents may be co-dispensed or sequentially dispensed. In a co-dispensed system, the oxidizing agent(s) and reducing agent(s) may be in a single phase. In one form of the co-dispensed system, the oxidizing agent(s) will be water soluble and the reducing agent(s) will be water insoluble and included within a single-phase. In a single-phase system, the reducing agent(s) and/or oxidizing agent(s) may be encapsulated in a material to provide physical separation of the two agents. The encapsulation may be broken via a mechanical means (i.e. brushing, gargling or other agitation of the oral cavity) to provide for the reducing agent(s) to neutralize the oxidizing agent(s). Non-limiting examples of encapsulating agents include gums, starches, polymers and other hydrophobic materials.

One non-limiting exemplary form of a co-dispensed system is when the oxidizing and reducing agents are in the form of toothpaste or a mouth rinse. Where the oxidizing agents and reducing agents are such that one is water soluble and the other is water insoluble, a single phase co-dispensed method of application is preferred.

In a sequentially dispensed system, the oxidizing agent(s) and its orally acceptable carrier(s) will be physically separated from the reducing agent(s) and its orally acceptable carrier(s) (two or more phase system). For example, a two or more cavity toothpaste tube, wherein the oxidizing agent(s)/orally acceptable carrier(s) are physically separated from reducing agent(s)/orally acceptable carrier(s) is one form of a sequentially dispensed system. In this system, the oxidizing agent(s)/orally acceptable carrier(s) and reducing agent(s)/orally acceptable carrier(s) are combined when the toothpaste enters the oral cavity. The oxidizing agent(s) provide the whitening and cleaning to the teeth and the reducing agent(s) neutralize/terminate the oxidization reaction to minimize gum damage. In another form of a sequential system, a tooth paste may include the oxidizing agent(s)/orally acceptable carrier(s), which is first applied to the oral cavity. This is followed by the application of a mouth rinse including reducing agent(s)/orally acceptable carrier(s) to neutralize/terminate the residual oxidizing agents from the toothpaste. With a sequential system, the oxidizing agent(s) and reducing agents(s) are generally not in a single phase. Hence, a water soluble oxidizing agent and a water soluble reducing agent may be used. Where both the oxidizing and reducing agents are water soluble, a two-phase sequential method of application is preferred.

The oxidizing agent(s) may be co-dispensed or sequentially dispensed in the form of a dental floss dispensed through a two-chamber dispenser. U.S. Pat. No. 6,705,328 discloses methods of impregnating and dispensing dental floss using novel dental floss dispensers and is incorporated by reference in its entirety herein.

In addition to the oxidizing agents and reducing agents described above, the present compositions may comprise additional components, which are described in the following paragraphs.

Orally Acceptable Carrier:

The orally acceptable carrier comprises one or more compatible solid or liquid filler diluents or encapsulating substances which are suitable for topical oral administration. By "compatible," as used herein, is meant that the components of the composition are capable of being commingled without interaction in a manner which would substantially reduce the composition's stability and/or efficacy.

The carriers or excipients of the present disclosure can include the usual and conventional components of dentifrices (including non-abrasive gels and gels for subgingival application), mouth rinses, mouth sprays, chewing gums, and lozenges (including breath mints) as more fully described hereinafter.

The choice of a carrier to be used is basically determined by the way the composition is to be introduced into the oral cavity. If a toothpaste (including tooth gels, etc.) is to be used, then a "toothpaste carrier" is chosen (e.g., abrasive materials, sudsing agents, binders, humectants, flavoring and sweetening agents, etc.) as disclosed in, e.g., U.S. Pat. No. 3,988,433, to Benedict. If a mouth rinse is to be used, then a "mouth rinse carrier" is chosen (e.g., water, flavoring and sweetening agents, etc.), as disclosed in, e.g., U.S. Pat. No. 3,988,433 to Benedict. Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al.; if a chewing gum is to be used, then a "chewing gum carrier" is chosen (e.g., gum base, flavoring and sweetening agents), as disclosed in, e.g., U.S. Pat. No. 4,083,955, to Grabenstetter et al. If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. Nos. 5,198,220 and 5,242,910, issued Mar. 30, 1993 and Sep. 7, 1993, respectively both to Damani. Carriers suitable for the preparation of compositions of the present disclosure are well known in the art. Their selection will depend on secondary considerations like taste, cost, and shelf stability, etc.

The compositions of the present disclosure may be in the form of non-abrasive gels, including subgingival gels, which may be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The compositions may comprise an anticaries agent (from about 0.05% to about 0.3% as fluoride ion), and an anticalculus agent (from about 0.1% to about 13%).

Preferred compositions of the present disclosure may also be in the form of dentifrices, such as toothpastes, tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the present disclosure are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred compositions of the present disclosure are dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and fast-dissolving solid forms including compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in U.S. patent application Ser. No. 08/253,890, filed Jun. 3, 1994, Brideau; U.S. Pat. Nos. 4,642,903; 4,946, 684; 4,305,502; 4,371,516; 5,188,825; 5,215,756; 5,298,261; 3,882, 228; 4,687, 662; 4,642,903.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: The Science and Practice of Pharmacy, 19$^{th}$ Ed., Vol. 11, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994.

In still another aspect, the disclosure comprises a dental implement impregnated with the present composition. The dental implement comprises an implement for contact with teeth and other tissues in the oral cavity, said implement being impregnated with a composition comprising the present oxidizing agent and reducing agent. The dental implement can be impregnated fibers including dental floss or tape, chips or strips and polymer fibers.

Types of carriers or oral care excipients which may be included in compositions of the present disclosure, along with specific non-limiting examples, are discussed in the following paragraphs.

Abrasives:

Dental abrasives, like the dental polishing agents, also cause a small amount of enamel erosion which is termed "polishing" action. The removal of plaque and calculus prevents caries and periodontal disease. The polishing of teeth removes stains from tooth surfaces, but has not been shown to improve dental health over and above the effects of the removal of plaque and calculus. Dental abrasives have a Mohs hardness ranging from 1.5 to 5.0, or 2.5 to 5.0, or 3.0 to 4.5, or 3.5 to 4.0. Typical dental abrasives are carbonates and pyrophosphates. Preferably, antioxidants that function as also abrasives should be used in the dental compositions disclosed herein. These antioxidants have the capacity to neutralize oxidizing agents in the subject oral cavity, clean the teeth and also abrade/polish the teeth.

Antioxidants that are also useful as abrasives are those discussed above in polymeric peel form. The peel of the fruit may be freeze dried and then reacted with carbonate to form polylimine carbonate. Polymeric cuteins of suitable peels are usually polyester polymers, like polylimones (artificial plastics from polylimone carbonate polymer) from the rind or peel/skin of the fruit (such as from oranges and corn). The cutein from fruits are typically polyesters of omega hydroxy acids and useful as abrasives if they have a Mohs hardness of less than or equal to 2.5 and preferably 1.5 to 2.5. Suberin is a waxy substance found in higher plants and is a main constituent of cork, such as cork oak. Suberins are divided into polyaromatic/polyaliphatic natural polymers, and may be used as abrasives that also function as antioxidants.

Dental abrasives useful in the topical, oral carriers of the compositions of the subject disclosure include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present disclosure are described in more detail in Wason, U.S. Pat. No. 4,340,583, issued Jul. 29, 1982; and in commonly-assigned U.S. Pat. No. 5,603, 920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued on Jul. 29, 1997, and U.S. Provisional Application Ser. No. 60/300,766, filed Jun. 25, 2001.

Mixtures of abrasives can be used such as mixtures of the various grades of silica with one or more fruit antioxidant abrasives listed above. The total amount of abrasive in dentifrice compositions of the present disclosure preferably range from about 6% to about 70% by weight; toothpastes preferably contain from about 10% to about 50% of abrasives, by weight of the composition. Solution, mouth spray, mouthwash and non-abrasive gel compositions of the present disclosure typically contain no abrasive.

Surfactants:

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. The present composition typically comprises an anionic surfactant at a level of from about 0.025% to about 9%, preferably from about 0.05% to about 5%, and most preferably from about 0.1% to about 1%.

Another preferred surfactant is one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate. This surfactant can be present in the compositions of the present disclosure from about 0.1% to about 2.5%, preferably from about 0.3% to about 2.5% and most preferably from about 0.5% to about 2.0% by weight of the total composition.

Preferred cationic surfactants useful in the present disclosure can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein. Cationic surfactants such as chlorhexidine, although suitable for use in the current disclosure, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present disclosure can be broadly defined as compounds produced by the condensation of alkylene oxide groups (hydrophilic in nature) with an organic hydrophobic compound which may be aliphatic or alkylaromatic in nature. Examples of suitable nonionic surfactants include the pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present disclosure can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

Anticalculus Agent:

The present compositions may also include an anticalculus agent, preferably a pyrophosphate ion source which is from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present disclosure, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used. The pyrophosphate salts are described in more detail in *Kirk-Othmer Encyclopedia of Chemical Technology*, Third Edition, Volume 17, Wiley-Interscience Publishers (1982).

Chelating Agents:

Another preferred optional agent is a chelating agent such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present disclosure.

Sodium and potassium citrate are the preferred alkali metal citrates, with sodium citrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present disclosure are about 0.1% to about 2.5%, preferably from about 0.5% to about 2.5% and more preferably from about 1.0% to about 2.5%. The tartaric acid salt chelating agent can be used alone or in combination with other optional chelating agents.

Other optional chelating agents can be used. Preferably these chelating agents have a calcium binding constant of about $10^1$ to $10^5$ provide improved cleaning with reduced plaque and calculus formation.

Still another possible group of chelating agents suitable for use in the present disclosure are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Fluoride Source:

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Thickening Agents:

In preparing toothpaste or gels, it is necessary to add some thickening material to provide a desirable consistency of the composition, to provide desirable active release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220, and 5,242,910, issued Mar. 30, 1993 and Sep. 7, 1993, respectively both to Damani, and U.S. Pat. No. 4,443,430, issued Apr. 17, 1984 to Mattei.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants:

Another optional component of the topical, oral carriers of the compositions of the present disclosure is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the present disclosure include edible polyhydric alcohols such as glycerin, sorbitol, xylitol, butylene glycol, polyethylene glycol, and propylene glycol, especially sorbitol and glycerin.

Flavoring and Sweetening Agents:

Flavoring agents can also be added to the compositions. Suitable flavoring agents include oil of wintergreen, oil of peppermint, oil of spearmint, clove bud oil, menthol, anethole, methyl salicylate, eucalyptol, *cassia*, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

In addition to flavoring and sweetening agents, coolants, salivating agents, warming agents, and numbing agents can be used as optional ingredients in compositions of the present disclosure. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Preferred salivating agents of the present disclosure include Jambu® manufactured by Takasago. Preferred warming agents include *capsicum* and nicotinate esters, such as benzyl nicotinate. Preferred numbing agents include benzocaine, lidocaine, clove bud oil, and ethanol.

Alkali Metal Bicarbonate Salt:

The present disclosure may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Miscellaneous Carriers:

Water employed in the preparation of commercially suitable oral compositions should preferably be of low ion content and free of organic impurities. Water generally comprises from about 5% to about 70%, and preferably from about 20% to about 50%, by weight of the aqueous compositions herein. These amounts of water include the free water which is added plus that which is introduced with other materials, such as with sorbitol.

Titanium dioxide may also be added to the present composition. Titanium dioxide is a white powder which adds opacity to the compositions. Titanium dioxide generally comprises from about 0.25% to about 5% by weight of the dentifrice compositions.

The pH of the present compositions is preferably adjusted through the use of buffering agents. Buffering agents, as used herein, refer to agents that can be used to adjust the pH of the compositions to a range of about pH 4.0 to about pH 10.0. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Other useful carriers include biphasic dentifrice formulations such as those disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849,213 and 4,528,180 to Schaeffer.

Other Active Agents:

The present disclosure may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bisbiquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium]alkanes as disclosed in U.S. Pat. No. 4,206,215, issued Jun. 3, 1980, to Bailey. Other antimicrobials such as copper bisglycinate, copper glysinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents, which provide anti-plaque benefits, may be present at levels of from about 0.01% to about 5.0%, by weight of the dentifrice composition.

Method of Use:

The present disclosure also relates to methods for cleaning and polishing teeth and reducing the incidence of stain, plaque, gingivitis and calculus on dental enamel while also minimizing damage to the gums.

The method of use herein comprises contacting a subject's dental enamel surfaces and oral mucosa with the oral compositions according to the present disclosure. The method of use may be by brushing with a dentifrice, rinsing with a dentifrice slurry or mouth rinse, or chewing a gum product. Other methods include contacting the topical oral gel, mouth spray, or other form with the subject's teeth and oral mucosa. The subject is any person or lower animal whose tooth surface contacts the oral composition.

It should be understood that the present disclosure relates not only to methods for delivering the present compositions to the oral cavity of a human, but also to methods of delivering these compositions to the oral cavity of other animals, e.g., household pets or other domestic animals, or animals kept in captivity.

For example, a method of use may include brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition including the present copolymer is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

Additional Aspects of the Disclosed Embodiments:

In accordance with the aspects of the disclosed embodiment, a dental cleaning composition is provided. The dental cleaning composition includes a substantially stoichiometric ratio of one or more oxidizing agents to one or more reducing agents in one or more orally acceptable carriers, wherein the substantially stoichiometric ratio of one or more oxidizing agents to one or more reducing agents is sufficient to neutralize the oxidizing agent in a subject oral cavity, and wherein the one or more oxidizing agents and one or more reducing agents are either co-dispensed or sequentially dispensed in the subject oral cavity.

In accordance with a first aspect of the dental cleaning composition the one or more oxidizing agents are chosen from potassium, ammonium, sodium, peroxides, metal chlorites, perborates, percarbonates, peroxyacids, persulfates, sodium pyrophosphate peroxyhydrate and combinations thereof.

In accordance with the first aspect of the dental cleaning composition the peroxides are chosen from hydrogen peroxide, urea peroxide and calcium peroxide.

In accordance with the first aspect of the dental cleaning composition the metal chlorites are chosen from calcium chlorite, barium chlorite, magnesium chlorite, lithium chlorite, sodium chlorite, and potassium chlorite.

In accordance with the first aspect of the dental cleaning composition the persulfate is lithium persulfate.

In accordance with the first aspect of the dental cleaning composition the perforates are perborate mono- and tetrahydrates.

In accordance with a second aspect of the dental cleaning composition the one or more reducing agents are chosen from lithium aluminium hydride, nascent hydrogen, sodium amalgam, sodium borohydride, tin(II) chloride, bismuth compounds, sulfite compounds, hydrazine, Lindlar catalyst, phosphites, hypophosphites, phosphorous acid, dithiothreitol, and iron(II) sulfate, antioxidant compounds and elements, and combinations thereof.

In accordance with the second aspect of the dental cleaning composition the antioxidant compounds and elements are chosen from coenzyme Q10, manganese, selenium, tin, bismuth, zinc, ascorbic acid (Vitamin C), melatonin, polyphenols (gallic acid, pyrogallol, quercetin, ethyl gallate, naringenin, luteolin, hesperidin, catechins), uric acid, lipoic acid, melatonin, glutathione, polyphenols, α-tocopherols and tocotrienols (Vitamin E), thiols, Vitamin A (retinol), carotenes, Vitamin D, ubiquinol (coenzyme Q), propyl gallate (PG, E310), tertiary butylhydroquinone (TBHQ), butylated hydroxyanisole (BHA, E320), butylated hydroxytoluene (BHT, E321), catechins, rosmarinic acid, cynarin, cyanidin 3-O-β-glucopyranoside, echinacoside, puerarin, oleuropein and combinations thereof.

In accordance with the second aspect of the dental cleaning composition the antioxidant compounds and elements are chosen from lemon peel powder, grapefruit peel powder, melon peel powder, honeydew peel powder, pomegranate peel powder, and *papaya* peel powder and combinations thereof. It is noted that the antioxidant compounds and elements may also function as abrasive and/or cleaning agents. It is further noted that the abrasive agents may have a Mohs hardness ranging from 1.5 to 2.5.

In accordance with the second aspect of the dental cleaning composition the antioxidant compounds and elements are dried fruits chosen from raisin, fig, dates, blueberry, cranberry, blackberry, prune, raspberry, strawberry, apple, pecan, cherry, plum, pear, guava, mango, grapes, blackcurrant, orange, peach, cantaloupe, apricots, kiwi, and combinations thereof.

In accordance with the second aspect of the dental cleaning composition the antioxidant compounds and elements are dried vegetables chosen from beet, red pepper, eggplant, brussels sprout, broccoli, cabbage, mushroom, asparagus, green pepper, cauliflower, spinach, carrot, chile pepper, sweet potato, radish, yellow onion, lettuce, potato, sweet corn, white onion, squash, celery, zucchini, romaine lettuce, green pea, beetroot, avocado, green, bean, cucumber, broccoli rape, corn, garlic, kale, iceberg lettuce, leaf lettuce, broccoli flowers, artichoke, alfalfa sprouts, cherry-tomato, chive, red bean, kidney bean, black bean, pinto bean, russet potato, asparagus, and combinations thereof.

In accordance with the second aspect of the dental cleaning composition the antioxidant compounds and elements are herbal botanical extracts chosen from green tea, black tea and combinations thereof.

In accordance with the second aspect of the dental cleaning composition the antioxidant compounds and elements are chosen from carotenoid terpenoids, flavonoid polyphenolics (flavones, flavonols, flavanones, flavanols and their polymers, isoflavone phytoestrogens, stilbenoids and anthocyanins), phenolic acids and their esters, other nonflavonoid phenolics, and other potential organic antioxidants, and combinations thereof.

In accordance with the second aspect of the dental cleaning composition the antioxidant compounds and elements are chosen from nuts, spices, herbs and combinations thereof. It is noted that the nuts are chosen from pecans, walnuts, hazelnuts, pistachio, almond, cashew nut, macadamia nut, peanuts and combinations thereof. It is noted that the spices are chosen from clove, cinnamon, oregano, turmeric, cumin, parsley, basil, curry powder, mustard seed, ginger, pepper, chili powder, paprika, garlic, coriander, onion, cardamom, and combinations thereof. It is noted that the herbs are chosen from sage, thyme, marjoram, tarragon, peppermint, oregano, savory, basil, dill weed and combinations thereof.

In accordance with a third aspect of the dental cleaning composition the one or more orally acceptable carriers are chosen from abrasives, surfactants, anticalculus agents, chelating agents, fluoride sources, thickening agents, humectants, alkali metal bicarbonate salt, miscellaneous carriers, other active agents and combinations thereof. It is noted that the abrasives are chosen from carbonates, pyrophosphates, polylimones, cuteins, suberins and combinations thereof. It is noted that the abrasives have a Mohs hardness ranging from 1.5 to 5.0. It is noted that the abrasives also function as antioxidant compounds.

In accordance with a fourth aspect of the dental cleaning composition the composition is in the form of chosen from a toothpaste, dentifrice, tooth powder, topical oral gel, mouth rinse, denture product, mouth spray, lozenge, oral tablet, chewing gum, impregnated dental implement, dental floss, and combinations thereof.

In accordance with the fifth aspect of the dental cleaning composition the composition provides enhanced cleaning, whitening and stain removal from teeth with minimal gum and enamel damage.

In accordance with the aspects of the disclosed embodiment, a method for cleaning teeth is provided. The method includes providing a dental cleaning composition including a substantially stoichiometric ratio of one or more oxidizing agents to one or more reducing agents in one or more orally acceptable carriers, and applying the dental cleaning composition to a subject oral cavity in a form chosen from a toothpaste, dentifrice, tooth powder, topical oral gel, mouth rinse, denture product, mouth spray, lozenge, oral tablet, or chewing gum, impregnated dental implement, dental floss, and combinations thereof, wherein the substantially stoichiometric ratio of one or more oxidizing agents to one or more reducing agents is sufficient to neutralize the oxidizing agent in the subject oral cavity, and wherein the one or more oxidizing agents and the one or more reducing agents of the dental cleaning composition are either co-dispensed or sequentially dispensed in the subject oral cavity.

In accordance with a first aspect of the method for cleaning teeth the one or more oxidizing agents are chosen from potassium, ammonium, sodium, peroxides, metal chlorites, perborates, percarbonates, peroxyacids, persulfates, sodium pyrophosphate peroxyhydrate and combinations thereof. It is noted that the peroxides are chosen from hydrogen peroxide, urea peroxide and calcium peroxide. It is noted that the metal chlorites are chosen from calcium chlorite, barium chlorite, magnesium chlorite, lithium chlorite, sodium chlorite, and potassium chlorite. It is noted that the persulfate is lithium persulfate. It is noted that the perforates are perborate mono- and tetrahydrates.

In accordance with a second aspect of the method for cleaning teeth the one or more reducing agents are chosen from lithium aluminium hydride, nascent hydrogen, sodium amalgam, sodium borohydride, tin(II) chloride, bismuth compounds, sulfite compounds, hydrazine, Lindlar catalyst, phosphites, hypophosphites, phosphorous acid, dithiothreitol, and iron(II) sulfate, antioxidant compounds and elements, and combinations thereof.

In accordance with the second aspect of the method for cleaning teeth, it is noted that the antioxidant compounds and elements are chosen from coenzyme Q10, manganese, selenium, tin, bismuth, zinc, ascorbic acid (Vitamin C), melatonin, polyphenols (gallic acid, pyrogallol, quercetin, ethyl gallate, naringenin, luteolin, hesperidin, catechins), uric acid, lipoic acid, melatonin, glutathione, polyphenols, α-tocopherols and tocotrienols (Vitamin E), thiols, Vitamin A (retinol), carotenes, Vitamin D, ubiquinol (coenzyme Q), propyl gallate (PG, E310), tertiary butylhydroquinone (TBHQ), butylated hydroxyanisole (BHA, E320), butylated hydroxytoluene (BHT, E321), catechins, rosmarinic acid, cynarin, cyanidin 3-O-β-glucopyranoside, echinacoside, puerarin, oleuropein and combinations thereof.

In accordance with the second aspect of the method for cleaning teeth, it is noted that the antioxidant compounds and elements are chosen from lemon peel powder, grapefruit peel powder, melon peel powder, honeydew peel powder, pomegranate peel powder, and *papaya* peel powder and combinations thereof. It is noted that the antioxidant compounds and elements also function as abrasive and/or cleaning agents. It is noted that the abrasive agents have a Mohs hardness ranging from 1.5 to 2.5.

In accordance with the second aspect of the method for cleaning teeth, the antioxidant compounds and elements are dried fruits chosen from raisin, fig, dates, blueberry, cranberry, blackberry, prune, raspberry, strawberry, apple, pecan, cherry, plum, pear, guava, mango, grapes, blackcurrant, orange, peach, cantaloupe, apricots, kiwi, and combinations thereof.

In accordance with the second aspect of the method for cleaning teeth, the antioxidant compounds and elements are dried vegetables chosen from beet, red pepper, eggplant, brussels sprout, broccoli, cabbage, mushroom, asparagus, green pepper, cauliflower, spinach, carrot, chile pepper, sweet potato, radish, yellow onion, lettuce, potato, sweet corn, white onion, squash, celery, zucchini, romaine lettuce, green pea, beetroot, avocado, green, bean, cucumber, broccoli rape, corn, garlic, kale, iceberg lettuce, leaf lettuce, broccoli flowers, artichoke, alfalfa sprouts, cherry-tomato, chive, red bean, kidney bean, black bean, pinto bean, russet potato, asparagus, and combinations thereof.

In accordance with the second aspect of the method for cleaning teeth, the antioxidant compounds and elements are herbal botanical extracts chosen from green tea, black tea and combinations thereof.

In accordance with the second aspect of the method for cleaning teeth, the antioxidant compounds and elements are chosen from carotenoid terpenoids, flavonoid polyphenolics (flavones, flavonols, flavanones, flavanols and their polymers, isoflavone phytoestrogens, stilbenoids and anthocyanins), phenolic acids and their esters, other nonflavonoid phenolics, and other potential organic antioxidants, and combinations thereof.

In accordance with the second aspect of the method for cleaning teeth, the antioxidant compounds and elements are chosen from nuts, spices, herbs and combinations thereof. It is noted that the nuts are chosen from pecans, walnuts, hazelnuts, pistachio, almond, cashew nut, macadamia nut, peanuts and combinations thereof. It is noted that the spices are chosen from clove, cinnamon, oregano, turmeric, cumin, parsley, basil, curry powder, mustard seed, ginger, pepper, chili powder, paprika, garlic, coriander, onion, cardamom, and combinations thereof. It is noted that the herbs are chosen from sage, thyme, marjoram, tarragon, peppermint, oregano, savory, basil, dill weed and combinations thereof.

In accordance with a third aspect of the method for cleaning teeth the one or more orally acceptable carriers are chosen from abrasives, surfactants, anticalculus agents, chelating agents, fluoride sources, thickening agents, humectants, alkali metal bicarbonate salt, miscellaneous carriers, other active agents and combinations thereof.

In accordance with the third aspect of the method for cleaning teeth the abrasives are chosen from carbonates, pyrophosphates, polylimones, cuteins, suberins and combinations thereof. It is noted that the abrasives have a Mohs hardness ranging from 1.5 to 5.0. It is noted that the abrasives also function as antioxidant compounds.

In accordance with a fourth aspect of the method for cleaning teeth the method provides enhanced cleaning, whitening and stain removal from teeth with minimal gum and enamel damage.

In accordance with the aspects of the disclosed embodiment, a method of making a dental cleaning composition is provided. The method includes providing a substantially stoichiometric ratio of one or more oxidizing agents, one or more reducing agents, and one or more orally acceptable carriers, mixing the one or more oxidizing agents into one or more orally acceptable carriers, mixing the one or more reducing agents into one or more orally acceptable carriers, and combining the mixture of the one or more oxidizing agents in one or more orally acceptable carriers and the mixture of the one or more reducing agents in one or more orally acceptable carriers in a form for either co-dispensing or sequentially dispensing in a subject oral cavity, wherein the substantially stoichiometric ratio of one or more oxidizing agents to one or more reducing agents is sufficient to neutralize the oxidizing agent in the subject oral cavity, and wherein the form for either co-dispensing or sequentially dispensing the dental cleaning composition to the subject oral cavity is chosen from a toothpaste, dentifrice, tooth powder, topical oral gel, mouth rinse, denture product, mouth spray, lozenge, oral tablet, or chewing gum, impregnated dental implement, dental floss, and combinations thereof.

In accordance with a first aspect of the method of making a dental cleaning composition the one or more oxidizing agents are chosen from potassium, ammonium, sodium, peroxides, metal chlorites, perborates, percarbonates, peroxyacids, persulfates, sodium pyrophosphate peroxyhydrate and combinations thereof.

In accordance with the first aspect of the method of making a dental cleaning composition the peroxides are chosen from hydrogen peroxide, urea peroxide and calcium peroxide. It is noted that the metal chlorites are chosen from calcium chlorite, barium chlorite, magnesium chlorite, lithium chlorite, sodium chlorite, and potassium chlorite. It is noted that the persulfate is lithium persulfate. It is noted that the perforates are perborate mono- and tetrahydrates.

In accordance with a second aspect of the method of making a dental cleaning composition the one or more reducing agents are chosen from lithium aluminium hydride, nascent hydrogen, sodium amalgam, sodium borohydride, tin(II) chloride, bismuth compounds, sulfite compounds, hydrazine, zinc-mercury amalgam, Lindlar catalyst, oxalic acid, formic acid, phosphites, hypophosphites, phosphorous acid, dithiothreitol, and iron(II) sulfate, antioxidant compounds and elements, and combinations thereof.

In accordance with the second aspect of the method of making a dental cleaning composition the antioxidant compounds and elements are chosen from coenzyme Q10, manganese, tin, bismuth, selenium, zinc, ascorbic acid (Vitamin C), melatonin, polyphenols (gallic acid, pyrogallol, quercetin, ethyl gallate, naringenin, luteolin, hesperidin, catechins), uric acid, lipoic acid, melatonin, glutathione, polyphenols, α-tocopherols and tocotrienols (Vitamin E), thiols, Vitamin A (retinol), carotenes, Vitamin D, ubiquinol (coenzyme Q), propyl gallate (PG, E310), tertiary butylhydroquinone (TBHQ), butylated hydroxyanisole (BHA, E320), butylated hydroxytoluene (BHT, E321), catechins, rosmarinic acid, cynarin, cyanidin 3-O-β-glucopyranoside, echinacoside, puerarin, oleuropein and combinations thereof.

In accordance with the second aspect of the method of making a dental cleaning composition the antioxidant compounds and elements are chosen from lemon peel powder, grapefruit peel powder, melon peel powder, honeydew peel powder, pomegranate peel powder, and *papaya* peel powder and combinations thereof. It is noted that the antioxidant compounds and elements also function as abrasive and/or cleaning agents. It is noted that the abrasive agents have a Mohs hardness ranging from 1.5 to 2.5.

In accordance with the second aspect of the method of making a dental cleaning composition the antioxidant compounds and elements are dried fruits chosen from raisin, fig, dates, blueberry, cranberry, blackberry, prune, raspberry, strawberry, apple, pecan, cherry, plum, pear, guava, mango, grapes, blackcurrant, orange, peach, cantaloupe, apricots, kiwi, and combinations thereof.

In accordance with the second aspect of the method of making a dental cleaning composition the antioxidant compounds and elements are dried vegetables chosen from beet, red pepper, eggplant, brussels sprout, broccoli, cabbage, mushroom, asparagus, green pepper, cauliflower, spinach, carrot, chile pepper, sweet potato, radish, yellow onion, lettuce, potato, sweet corn, white onion, squash, celery, zucchini, romaine lettuce, green pea, beetroot, avocado, green, bean, cucumber, broccoli rape, corn, garlic, kale, iceberg lettuce, leaf lettuce, broccoli flowers, artichoke, alfalfa sprouts, cherry-tomato, chive, red bean, kidney bean, black bean, pinto bean, russet potato, asparagus, and combinations thereof.

In accordance with the second aspect of the method of making a dental cleaning composition the antioxidant compounds and elements are herbal botanical extracts chosen from green tea, black tea and combinations thereof.

In accordance with the second aspect of the method of making a dental cleaning composition the antioxidant compounds and elements are chosen from carotenoid terpenoids, flavonoid polyphenolics (flavones, flavonols, flavanones, flavanols and their polymers, isoflavone phytoestrogens, stilbenoids and anthocyanins), phenolic acids and their esters, other nonflavonoid phenolics, and other potential organic antioxidants, and combinations thereof.

In accordance with the second aspect of the method of making a dental cleaning composition the antioxidant compounds and elements are chosen from nuts, spices, herbs and combinations thereof. It is noted that the nuts are chosen from pecans, walnuts, hazelnuts, pistachio, almond, cashew nut, macadamia nut, peanuts and combinations thereof. It is noted that the spices are chosen from clove, cinnamon, oregano, turmeric, cumin, parsley, basil, curry powder, mustard seed, ginger, pepper, chili powder, paprika, garlic, coriander, onion, cardamom, and combinations thereof. It is noted that the herbs are chosen from sage, thyme, marjoram, tarragon, peppermint, oregano, savory, basil, dill weed and combinations thereof.

In accordance with a third aspect of the method of making a dental cleaning composition the one or more one or more orally acceptable carriers are chosen from abrasives, surfactants, anticalculus agents, chelating agents, fluoride sources, thickening agents, humectants, alkali metal bicarbonate salt, miscellaneous carriers, other active agents and combinations thereof.

In accordance with the third aspect of the method of making a dental cleaning composition the abrasives are chosen from carbonates, pyrophosphates, polylimones, cuteins, suberins and combinations thereof. It is noted that the abrasives have a Mohs hardness ranging from 1.5 to 5.0. It is noted that the abrasives also function as antioxidant compounds.

In accordance with a fourth aspect of the method of making a dental cleaning composition the method provides enhanced cleaning, whitening and stain removal from teeth with minimal gum and enamel damage.

In accordance with the aspect of the disclosed embodiment, a dental cleaning composition is provided. The composition includes 0.5 to 90 wt. % of one or more reducing agents in one or more orally acceptable carriers, wherein the one or more reducing agents are chosen from food grade antioxidants.

In accordance with a first aspect of the dental cleaning composition the one or more food grade antioxidants are chosen from coenzyme Q10, manganese, tin, bismuth, selenium, zinc, ascorbic acid (Vitamin C), melatonin, polyphenols (gallic acid, pyrogallol, quercetin, ethyl gallate, naringenin, luteolin, hesperidin, catechins), uric acid, lipoic acid, melatonin, glutathione, polyphenols, α-tocopherols and tocotrienols (Vitamin E), thiols, Vitamin A (retinol), carotenes, Vitamin D, ubiquinol (coenzyme Q), propyl gallate (PG, E310), tertiary butylhydroquinone (TBHQ), butylated hydroxyanisole (BHA, E320), butylated hydroxytoluene (BHT, E321), catechins, rosmarinic acid, cynarin, cyanidin 3-O-β-glucopyranoside, echinacoside, puerarin, oleuropein and combinations thereof.

In accordance with a second aspect of the dental cleaning composition the one or more food grade antioxidants are chosen from lemon peel powder, grapefruit peel powder, melon peel powder, honeydew peel powder, pomegranate peel powder, and *papaya* peel powder and combinations thereof.

In accordance with the second aspect of the dental cleaning composition the one or more food grade antioxidants function as abrasive and/or cleaning agents. It is noted that the abrasive agents have a Mohs hardness ranging from 1.5 to 2.5.

In accordance with a third aspect of the dental cleaning composition the one or more food grade antioxidants are dried fruits chosen from raisin, fig, dates, blueberry, cranberry, blackberry, prune, raspberry, strawberry, apple, pecan, cherry, plum, pear, guava, mango, grapes, blackcurrant, orange, peach, cantaloupe, apricots, kiwi, and combinations thereof.

In accordance with a fourth aspect of the dental cleaning composition the one or more food grade antioxidants are dried vegetables chosen from beet, red pepper, eggplant, brussels sprout, broccoli, cabbage, mushroom, asparagus, green pepper, cauliflower, spinach, carrot, chili pepper, sweet potato, radish, yellow onion, lettuce, potato, sweet corn, white onion, squash, celery, zucchini, romaine lettuce, green pea, beetroot, avocado, green, bean, cucumber, broccoli rape, corn, garlic, kale, iceberg lettuce, leaf lettuce, broccoli flowers, artichoke, alfalfa sprouts, cherry-tomato, chive, red bean, kidney bean, black bean, pinto bean, russet potato, asparagus, and combinations thereof.

In accordance with a fifth aspect of the dental cleaning composition the one or more food grade antioxidants are herbal botanical extracts chosen from green tea, black tea and combinations thereof.

In accordance with a sixth aspect of the dental cleaning composition the one or more food grade antioxidants are chosen from carotenoid terpenoids, flavonoid polyphenolics (flavones, flavonols, flavanones, flavanols and their polymers, isoflavone phytoestrogens, stilbenoids and anthocyanins), phenolic acids and their esters, other nonflavonoid phenolics, and other potential organic antioxidants, and combinations thereof.

In accordance with a seventh aspect of the dental cleaning composition the one or more food grade antioxidants are chosen from nuts, spices, herbs and combinations thereof.

In accordance with the seventh aspect of the dental cleaning composition the nuts are chosen from pecans, walnuts, hazelnuts, pistachio, almond, cashew nut, macadamia nut, peanuts and combinations thereof.

In accordance with the seventh aspect of the dental cleaning composition the spices are chosen from clove, cinnamon, oregano, turmeric, cumin, parsley, basil, curry powder, mustard seed, ginger, pepper, chili powder, paprika, garlic, coriander, onion, cardamom, and combinations thereof.

In accordance with the seventh aspect of the dental cleaning composition the herbs are chosen from sage, thyme, marjoram, tarragon, peppermint, oregano, savory, basil, dill weed and combinations thereof.

In accordance with an eighth aspect of the dental cleaning composition the one or more one or more orally acceptable carriers are chosen from abrasives, surfactants, anticalculus agents, chelating agents, fluoride sources, thickening agents, humectants, alkali metal bicarbonate salt, miscellaneous carriers, other active agents and combinations thereof.

In accordance with the eighth aspect of the dental cleaning composition the abrasives are chosen from carbonates, pyrophosphates, polylimones, cuteins, suberins and combinations thereof. It is noted that the abrasives have a Mohs hardness ranging from 1.5 to 5.0. It is noted that the abrasives also function as antioxidant compounds.

In accordance with a ninth aspect of the dental cleaning composition the composition is in the form of chosen from a toothpaste, dentifrice, tooth powder, topical oral gel, mouth rinse, denture product, mouth spray, lozenge, oral tablet, chewing gum, impregnated dental implement, dental floss, and combinations thereof.

In accordance with a tenth aspect of the dental cleaning composition the composition provides enhanced cleaning, whitening and stain removal from teeth with minimal gum and enamel damage.

It is noted, as can be seen above, that the embodiments provide dental cleaning compositions, methods of using and methods of using such compositions which minimize gum damage in the oral cavity. In one form, the dental cleaning composition includes a substantially stoichiometric ratio of one or more oxidizing agents to one or more reducing agents in one or more one or more orally acceptable carriers; where the substantially stoichiometric ratio of one or more oxidizing agents to one or more reducing agents is sufficient to neutralize the oxidizing agent in a subject oral cavity; and where the one or more oxidizing agents and one or more reducing agents are either co-dispensed or sequentially dispensed in the subject oral cavity.

The following examples will more fully illustrate the embodiments of the present disclosure and are not to be construed as limiting. All parts, percentages and proportions referred to herein and in the appended claims are by weight of the total composition unless otherwise stated.

EXAMPLES

Example 1

This example provides illustrative compositions of a first composition which is a viscous gel and a second composition which is a dispersion of lemon dust powder in glycerine. The two compositions may be co-dispensed or sequentially dispensed.

The first oxidizing composition components include 88 wt. % water, Poloxamer 407 5.0 wt. %, hydrogen peroxide at 3 wt. %, glycerin at 3 wt. %, and a sufficient amount to make a total of 100 wt. % of phosphoric acid/water (q.s.). The viscosity of the first oxidizing composition is greater than 250,000 cP with a pH equal to 4.0. The first composition is in the form of a peroxide gel or cream.

The second reducing composition components include 32 wt. % lemon peel dust and 67 wt. % glycerine, water/sodium hydroxide solution (q.s.,) in a rinse or gel form. The pH of the second composition is 4.5-5.0.

Example 2

Example 2 provides an illustrative composition of a viscous gel which is first applied to the gums for protection and is illustrative of sequential dispensing of oxidizing agent and reducing agent.

The first composition applied to the gums for protection includes 68 wt. % glycerine and 32 wt. % grape fruit peel powder.

The second composition is a professionally applied 30 wt. % hydrogen peroxide solution for dental office application in a rinse/liquid form. The pH of the rinse is buffered to 4-5. The sequential dispensing helps prevent sensitization of the subject's gums.

Example 3

Example 3 provides an illustrative composition of a mouth rinse which most preferably post applied after brightening with tooth whitening toothpaste. It could however be applied before brushing with a tooth whitening toothpaste.

The composition includes sorbitol solution in water (88 wt. %/12 wt. %) and 60 wt % of total composition, ascorbic acid at 5 wt. %, ascorbyl glycoside at 5 wt. %, propylene glycol at 25 wt. %, and water at 5 wt. %. The pH of the subject oral cavity after brushing and before rinsing with the above composition is 7 to 9. The pH of the subject oral cavity after brushing and rinsing with the above composition is 4 to 7.

Example 4

This example provides an example of an antioxidant toothpaste combining high levels antioxidant type abrasives and regular type abrasives.

The first composition includes 68 wt. % glycerine and 32 wt. % lemon peel dust (antioxidant abrasive composition).

The second composition include 10 wt. % sodium bicarbonate, 35 wt. % sorbitol, 3 wt. % sodium lauryl sulfate, 0.8 wt. % cellulose gum, 0.5 wt. % menthol. 0.3 wt % sodium fluoride and a sufficient amount to make a total of 100 wt. % of water (q.s.) (regular abrasive composition).

According to the present disclosure, an advantageous dental cleaning composition comprises a substantially stoichiometric ratio of one or more oxidizing agents to one or more reducing agents in one or more one or more orally acceptable carriers; wherein the substantially stoichiometric ratio of one or more oxidizing agents to one or more reducing agents is sufficient to neutralize the oxidizing agent in a subject oral cavity; and wherein the one or more oxidizing agents and one or more reducing agents are either co-dispensed or sequentially dispensed in the subject oral cavity. The resulting pH in the oral cavity will be in the range of 4 to 8.

Another aspect of the present disclosure relates to an advantageous dental cleaning composition comprising: 0.5 to 90 wt. % of one or more reducing agents in one or more orally acceptable carriers, wherein the one or more reducing agents are chosen from good grade antioxidants.

A further aspect of the present disclosure relates to an advantageous method for cleaning teeth comprising: providing a dental cleaning composition including a substantially stoichiometric ratio of one or more oxidizing agents to one or more reducing agents in one or more orally acceptable carriers; and applying the dental cleaning composition to a subject oral cavity in a form chosen from a toothpaste, dentifrice, tooth powder, topical oral gel, mouth rinse, denture product, mouth spray, lozenge, oral tablet, or chewing gum, impregnated dental implement, dental floss, and combinations thereof; wherein the substantially stoichiometric ratio of one or more oxidizing agents to one or more reducing agents is sufficient to neutralize the oxidizing agent in the subject oral cavity; and wherein the one or more oxidizing agents and the one or more reducing agents of the dental cleaning composition are either co-dispensed or sequentially dispensed in the subject oral cavity.

Another aspect of the present disclosure relates to an advantageous method of making a dental cleaning composition comprising: providing a substantially stoichiometric ratio of one or more oxidizing agents, one or more reducing agents, and one or more orally acceptable carriers; mixing the one or more oxidizing agents into one or more orally acceptable carriers; mixing the one or more reducing agents into one or more orally acceptable carriers; and combining the mixture of the one or more oxidizing agents in one or more orally acceptable carriers and the mixture of the one or more reducing agents in one or more orally acceptable carriers in a form for either co-dispensing or sequentially dispensing in a subject oral cavity; wherein the substantially stoichiometric ratio of one or more oxidizing agents to one or more reducing agents is sufficient to neutralize the oxidizing agent in the subject oral cavity; and wherein the form for either co-dispensing or sequentially dispensing the dental cleaning composition to the subject oral cavity is chosen from a toothpaste, dentifrice, tooth powder, topical oral gel, mouth rinse, denture product, mouth spray, lozenge, oral tablet, or chewing gum, impregnated dental implement, dental floss, and combinations thereof.

These and other features and attributes of the disclosed dental cleaning compositions and methods of making the dental cleaning compositions of the present disclosure and their advantageous applications and/or uses will be apparent from the detailed description which follows, particularly when read in conjunction with the enclosed examples.

Applicants have attempted to disclose all embodiments and applications of the disclosed subject matter that could be reasonably foreseen. However, there may be unforeseeable, insubstantial modifications that remain as equivalents. While the present disclosure has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated.

It should be understood that the foregoing description is only illustrative of the embodiments. Various alternatives and modifications can be devised by those skilled in the art without departing from the embodiments. Accordingly, the present embodiments are intended to embrace all such alternatives, modifications and variances that fall within the scope of the appended claims.

What is claimed is:

1. A dental cleaning composition comprising: 32 to 90 wt. % of one or more reducing agents in one or more orally acceptable carriers, wherein the one or more reducing agents are selected from the group consisting of melon peel powder, honeydew peel powder, papaya peel powder and combinations thereof,
   wherein the one or more one or more orally acceptable carriers are chosen from abrasives, surfactants, anticalculus agents, chelating agents, fluoride sources, thickening agents, humectants, alkali metal bicarbonate salt, miscellaneous carriers, other active agents and combinations thereof, and
   wherein the composition provides enhanced cleaning, whitening and stain removal from teeth with minimal gum and enamel damage.

2. The composition of claim 1, wherein the one or more food grade antioxidants are chosen from coenzyme Q10, manganese, iodide selenium, zinc, ascorbic acid (Vitamin C), melatonin, polyphenols (gallic acid, pyrogallol, quercetin, ethyl gallate, naringenin, luteolin, hesperidin, catechins), uric acid, lipoic acid, melatonin, glutathione, polyphenols, α-tocopherols and tocotrienols (Vitamin E), thiols, Vitamin A (retinol), carotenes, Vitamin D, ubiquinol (coenzyme Q), propyl gallate (PG, E310), tertiary butylhydroquinone (TBHQ), butylated hydroxyanisole (BHA, E320), butylated hydroxytoluene (BHT, E321), catechins, rosmarinic acid, cynarin, cyanidin 3-O-β-glucopyranoside, echinacoside, puerarin, oleuropein and combinations thereof.

3. The composition of claim 1, wherein the one or more reducing agents function as abrasive and/or cleaning agents.

4. The composition of claim 3, wherein the abrasive agents have a Mohs hardness ranging from 1.5 to 2.5.

5. The composition of claim 1, wherein the one or more food grade antioxidants are dried fruits chosen from raisin, fig, dates, blueberry, cranberry, blackberry, prune, raspberry, strawberry, apple, pecan, cherry, plum, pear, guava, mango, grapes, blackcurrant, orange, peach, cantaloupe, apricots, kiwi, and combinations thereof.

6. The composition of claim 1, wherein the one or more food grade antioxidants are dried vegetables chosen from beet, red pepper, eggplant, brussels sprout, broccoli, cabbage, mushroom, asparagus, green pepper, cauliflower, spinach, carrot, chile pepper, sweet potato, radish, yellow onion, lettuce, potato, sweet corn, white onion, squash, celery, zucchini, romaine lettuce, green pea, beetroot, avocado, green, bean, cucumber, broccoli rape, corn, garlic, kale, iceberg lettuce, leaf lettuce, broccoli flowers, artichoke, alfalfa sprouts, cherry-tomato, chive, red bean, kidney bean, black bean, pinto bean, russet potato, asparagus, and combinations thereof.

7. The composition of claim 1, wherein the one or more food grade antioxidants are herbal botanical extracts chosen from green tea, black tea and combinations thereof.

8. The composition of claim 1, wherein the one or more food grade antioxidants are chosen from carotenoid terpenoids, flavonoid polyphenolics (flavones, flavonols, flavanones, flavanols and their polymers, isoflavone phytoestrogens, stilbenoids and anthocyanins), phenolic acids and their esters, other nonflavonoid phenolics, and other potential organic antioxidants, and combinations thereof.

9. The composition of claim 1, wherein the one or more food grade antioxidants are chosen from nuts, spices, herbs and combinations thereof.

10. The composition of claim 9, wherein the nuts are chosen from pecans, walnuts, hazelnuts, pistachio, almond, cashew nut, macadamia nut, peanut butter and combinations thereof.

11. The composition of claim 9, wherein the spices are chosen from clove, cinnamon, oregano, turmeric, cumin, parsley, basil, curry powder, mustard seed, ginger, pepper, chili powder, paprika, garlic, coriander, onion, cardamom, and combinations thereof.

12. The composition of claim 9, wherein the herbs are chosen from sage, thyme, marjoram, tarragon, peppermint, oregano, savory, basil, dill weed and combinations thereof.

13. The composition of claim 1, wherein the abrasives are chosen from carbonates, pyrophosphates, polylimones, cuteins, suberins and combinations thereof.

14. The composition of claim 13, wherein the abrasives have a Mohs hardness ranging from 1.5 to 5.0.

15. The composition of claim 14, wherein the abrasives also function as antioxidant compounds.

16. The composition of claim 1, wherein the composition is in the form of chosen from a toothpaste, dentifrice, tooth powder, topical oral gel, mouth rinse, denture product, mouth spray, lozenge, oral tablet, chewing gum, impregnated dental implement, dental floss, and combinations thereof.

17. The composition of claim 1 comprising about 32 wt. % of one or more reducing agents.

* * * * *